United States Patent [19]

Lee

[11] 3,996,341
[45] Dec. 7, 1976

[54] PROCESS FOR PURIFYING TRIOCTYL PHOSPHATE AND USE THEREFOR

[75] Inventor: Nathan Dean Lee, Lambertville, N.J.

[73] Assignee: FMC Corporation, Philadelphia, Pa.

[22] Filed: Apr. 30, 1975

[21] Appl. No.: 573,099

[52] U.S. Cl. .................................. 423/589; 260/990
[51] Int. Cl.² ...................... C01B 15/02; C07F 9/02
[58] Field of Search .................... 260/990; 423/589; 210/41

[56] References Cited

UNITED STATES PATENTS

| 2,537,655 | 1/1951 | Dawsey et al. | 423/589 |
| 2,573,658 | 10/1951 | Weesner | 260/990 |
| 2,818,420 | 12/1957 | Dejonge | 260/990 |
| 3,328,128 | 6/1967 | Käbisch | 423/589 |
| 3,649,721 | 3/1972 | Burrous et al. | 260/990 |
| 3,706,823 | 12/1972 | Rampy et al. | 260/990 |

FOREIGN PATENTS OR APPLICATIONS

| 459,310 | 1/1937 | United Kingdom | 260/990 |

Primary Examiner—Oscar R. Vertiz
Assistant Examiner—Wayne A. Langel

[57] ABSTRACT

Process for purifying trioctyl phosphate containing emulsifier impurities comprising alkali metal salts of dioctyl phosphoric acid and monooctyl phosphoric acid by contacting the trioctyl phosphate with a mineral acid to neutralize the emulsifier impurities and to provide a two-phase system having an organic phase and an aqueous phase wherein the pH value of the aqueous phase is below 3.0, separating the organic phase from the aqueous phase, dehydrating the organic phase, and removing neutralized impurities by absorption on an absorbent material leaving a substantially pure trioctyl phosphate having an interfacial tension of about 18 to about 24 dynes/cm. The purified trioctyl phosphate has exceptional utility as a solvent in the anthraquinone process for producing hydrogen peroxide.

6 Claims, No Drawings

PROCESS FOR PURIFYING TRIOCTYL PHOSPHATE AND USE THEREFOR

This invention relates to a process for purifying trioctyl phosphate containing emulsifier impurities and to the use of the purified trioctyl phosphate as a solvent in the manufacture of hydrogen peroxide by the alternate oxidation and reduction of substituted anthraquinones.

It is known that anthraquinone compounds, that is, ethylanthraquinone, and their tetrahydro derivatives can be used as working compounds in a process for producing hydrogen peroxide. In this process, commonly known as the anthraquinone process, an anthraquinone working compound is dissolved in a suitable solvent, or mixture of solvents to form an anthraquinone working solution. The working solution thus obtained is hydrogenated in the presence of a catalyst to convert the anthraquinone to the corresponding anthrahydroquinone. The anthrahydroquinone is then oxidized by treatment with a gas containing oxygen whereby the anthraquinone is regenerated and hydrogen peroxide is produced. The hydrogen peroxide product is then extracted from the working solution with an aqueous solvent, preferably water. Extraction is normally carried out in a vertical column with the aqueous solvent as the aqueous extracting phase moving downwardly, countercurrently to the upwardly moving organic phase (working solution) containing the hydrogen peroxide. A cyclic process is provided by returning the working solution after extraction of the hydrogen peroxide to the hydrogenation stage and repeating the steps described above.

In the anthraquinone process it is important that the working solution meet certain viscosity and density requirements while maintaining the working compound in solution for efficient operation of all process steps in order to produce as great a yield of hydrogen peroxide as possible. Low viscosity is important for mechanical reasons, that is, for cycling the working compound through the reaction equipment. In addition, the density of the working solution must be substantially different from the density of the aqueous solvent in order to facilitate efficient extraction of hydrogen peroxide.

Various working solutions have been proposed which contain special solvents or solvent mixtures with selective dissolving abilities for the anthraquinone and/or anthrahydroquinone forms of the working compound. The anthraquinone solvents normally employed have been $C_8$ to $C_{17}$ ketone or xylene and $C_5$ to $C_{12}$ alcohol, benzene or alkylbenzene, and polyalkylated benzene having a total of 9 to 11 carbon atoms.

Trisubstituted organic esters of phosphoric acid have been proposed as solvents for the anthrahydroquinone form of the working compound, wherein the substituents may be alkyl or aryl groups. Typically useful phosphates are trioctyl phosphate, tributyl phosphate, diphenyloctyl phosphate, diphenylcresyl phosphate and tricresyl phosphate. These phosphates and their use in the anthraquinone process are described in U.S. Pat. No. 2,537,655 to Dawsey et al, and U.S. Pat. No. 3,328,128 to Kabisch.

Even though trisubstituted organic esters of phosphoric acid have been proposed as solvents for the anthrahydroquinone form of the working compond, with trioctyl phosphate as the preferred solvent, use of commercial grade or technical grade trioctyl phosphate as the anthrahydroquinone solvent has not been possible. Commercial and technical grade trioctyl phosphate contains low levels of emulsifier impurities, that is emulsification agents, which impurities render extraction of hydrogen peroxide by phase separation between the aqueous solvent and the working solution in the extractor impossible. It has therefore been necessary to employ costly preliminary purification methods in an effort to remove the emulsifier impurities. The purification methods employed, however, have heretofore been extremely time consuming and inefficient, resulting in losses of as much as 30% trioctylphosphate, thus contributing to the premium price paid for purified material. In addition, the purified material is somewhat viscous and often causes emulsification problems because of incomplete removal of the emulsifier impurities. For example, the interfacial tension of commercial grade trioctyl phosphate, which is a convenient means for determining the presence of emulsifier impurities, is generally about 5 to 7 dynes/cm. Trioctyl phosphates having such low interfacial tensions are completely unacceptable as solvents for the anthrahydroquinone form of the working compound; the minimum interfacial tension required is about 18 dynes/cm. These commercial grade materials have been heretofore upgraded to about 10 to 21 dynes/cm with concomitant losses of substantial amounts of trioctyl phosphate. It has therefore remained desirable to prepare purified trioctyl phosphate and in particular a trioctyl phosphate solvent which satisfies the varied requirements for the anthraquinone process in an efficient, effective and inexpensive manner.

A process has been unexpectedly discovered for purifying trioctyl phosphate containing emulsifier impurities comprising alkaline metal salts of dioctyl phosphoric acid and monooctyl phosphoric acid which comprises: contacting said trioctyl phosphate with a sufficient amount of an aqueous mineral acid solution to neutralize the emulsifier impurities and to provide a two-phase system having an organic phase and an aqueous phase wherein the pH value of the aqueous phase is between 0.5 and 3.0; separating the organic phase from the aqueous phase and removing entrained and dissolved water from the organic phase which phase contains trioctyl phosphate and neutralized impurities comprising dioctyl phosphoric acid and monooctyl phosphoric acid; contacting the organic phase with an absorbent material selected from the group consisting of activated alumina, silica gel, high surface area silica, zeolites, and activated magnesia whereby the neutralized impurities are absorbed leaving a substantially pure trioctyl phosphate having an interfacial tension of about 18 to about 24 dynes/cm.

Trioctyl phosphate is purified by the process of this invention in a highly effective and efficient manner, thus substantially reducing the premium price paid for purified material. In view of the high purity of the trioctyl phosphate product, as demonstrated by the extremely high interfacial tension measurements, the purified trioctyl phosphates of this invention have exceptional utility in the anthraquinone process for producing hydrogen peroxide, resulting in the expeditious extraction of hydrogen peroxide from the working solution.

The interfacial tension measurements given herein have been determined by the American Society for Testing Materials (ASTM) Designation D-971. This test method is a procedure for measuring, under nonequilibrium conditions, the interfacial tension of mineral oils against water at a temperature of 25° ± 1° C.

According to the process of the invention, trioctyl phosphate containing emulsifier impurities comprising alkali metal salts (normally sodium or potassium) of dioctyl phosphoric acid and monooctyl phosphoric acid is contacted with a sufficient amount of an aqueous mineral acid solution to neutralize the emulsifier impurities. Preferred mineral acids are sulfuric acid, phosphoric acid and nitric acid. Neutralization must be performed until the pH value of the aqueous phase remains between 0.5 and 3.0, and preferably between 2.2 and 2.7 to permit completion of the neutralization reaction. By keeping the pH value of the aqueous phase below 3 a distinct phase system having a sharp interface between the organic phase and the aqueous phase is provided. If the pH value of the aqueous phase is above 3.0, separation between the aqueous phase and organic phase is not achieved. Acid strength is not critical even though dilute acidic solutions are preferred over concentrated acidic solutions for handling reasons, with use of 0.01 to 0.001 moles of acid per liter of water preferred.

Contacting is performed in a manner which provides for the intimate mixing of the two phases so that thorough neutralization and extraction of the salts from the organic phase into the inorganic aqueous phase is achieved. Conventional contacting procedures, such as stirring and countercurrent contacting may be employed. The temperature of the reaction mixture during contacting is not critical with temperatures from 20° to 40° C being preferred.

Following neutralization of the emulsifier impurities, the organic phase is permitted to separate from the aqueous phase. The resulting clear aqueous phase is discarded, and the turbid organic phase containing trioctyl phosphate and neutralized impurities comprising dioctyl phosphoric acid and monooctyl phosphoric acid is dehydrated by conventional procedures to remove both entrained and dissolved water. The turbid organic phase contains about 0.25 to about 1.0 volume percent entrained water and up to 2 weight percent dissolved water. Dehydration is preferably performed by vacuum evaporation or by contacting the organic phase with a suitable desiccant, such as, calcium chloride, zinc chloride and anhydrous sodium sulfate, or by passing the organic phase through a conventional coalescing filter. Dehydration is essential to remove both the entrained and dissolved water from the organic phase in order to have effective utilization of the absorbent material for absorbing the neutralized impurities since the absorbent material may competitively function as a desiccant or drying agent.

After the entrained and dissolved water are removed from the organic phase, the organic phase is contacted with an absorbent material which selectively absorbs the neutralized impurities leaving a substantially pure trioctyl phosphate. The preferred absorbent materials are activated alumina, either in granular or spherical form, silica gel or high surface area silica (silicone dioxide), zeolites (natural or artificial), and activated magnesia (magnesium oxide). If this step is not performed, the alkali metal salts of dioctyl phosphoric acid and monooctyl phosphoric acid could reform when the trioctyl phosphate is contacted with a moderately alkaline system, thus substantially decreasing trioctyl phosphate interfacial tension measurements.

Contacting may be performed by conventional procedures, such as by adding the absorbent material to the organic phase followed by removing the absorbent material by conventional filtration methods. Alternately, the organic phase can be passed through a bed or column containing the absorbent material. When employing a bed or column containing the absorbent material, the absorbent material has a preferred size of 8, −50 (U.S. Standard Sieve).

The purified trioctyl phosphate solvent of this invention is particularly useful in processes for preparing hydrogen peroxide by the alternate reduction and oxidation of a working solution containing a substituted anthraquinone working compound dissolved in a mixed solvent containing an anthraquinone solvent and the purified trioctyl phosphate as the anthrahydroquinone solvent. When employing the purified trioctyl phosphate of this invention, which has an interfacial tension of about 18 to about 24 dynes/cm as an essential component of the working solution, the resulting working solution has an interfacial tension greater than 20 dynes/cm. This working solution has high dissolving power for both the anthraquinone and anthrahydroquinone forms of the working compound, low viscosity and therefore the ability to be circulated easily through the process, and high interfacial tension thereby facilitating efficient extraction of the hydrogen peroxide product from the working solution.

Use of purified trioctyl phosphate prepared by the process of this invention in a working solution as a solvent for the anthrahydroquinone form of the working compound also permits the use of an aqueous solvent during extraction having a broad pH range, preferably 0.1 to 5.0, which pH range favors hydrogen peroxide removal and stability without concomitant emulsification problems.

The working solution can contain the heretofore used anthraquinone working compounds, such as the alkyl anthraquinones, the anthraquinone carboxylic acid esters, the anthraquinone sulfonic acid esters, the halogenated anthraquinones, and the other prior art anthraquinones used in the anthraquinone process. Particularly useful anthraquinones are 2-ethylanthraquinone, tetrahydroethylanthraquinone, tert.-butylanthraquinone and amylanthraquinone. These working compounds are dissolved in one or more mixed solvents for the anthraquinone forms of the working compound such as $C_8$ to $C_{17}$ ketone or xylene and $C_5$ to $C_{12}$ alcohol, benzene or alkyl benzene and the like. A particularly useful solvent is polyalkylated benzenes having a total of 9 to 11 carbon atoms, such as trimethyl, methylethyl, methylbutyl, tetramethyl and the like benzenes.

The ratio of anthraquinone solvent to the purified trioctyl phosphate solvent may be varied within reasonably broad limits, and other solvents and/or inert substances may be added to the solvent mixture. Particularly useful solvent combinations are those in which the ratio of anthraquinone solvent to anthrahydroquinone solvent, that is of anthraquinone solvent to the trioctyl phosphate solvent is about 60 to about 85 volumes of the former to 40 to 15 volumes of the latter. The solvents are used in the working solution in an amount of at least about 37.5% by volume thereof, that is in an amount to provide at least about 15% by volume of the trioctyl phosphate. Use of less solvent causes the resulting working solution to have properties which make it difficult to process. The maximum amounts which may be used are dictated by economic considerations.

Alternate to the procedure of employing purified trioctyl phosphate in the working solution, the working solution may be prepared by dissolving the substituted anthraquinone working compound in a working solvent consisting essentially of an anthraquinone solvent and an impure trioctyl phosphate solvent containing emulsifier impurities comprising the alkali metal salts of dioctyl phosphoric acid and monooctyl phosphoric acid. The impure working solution is then purified by contacting the working solution with a sufficient amount of an aqueous sulfuric acid or phosphoric acid solution to neutralize the emulsifier impurities and to provide a two-phase system having an organic phase containing the working solution and an aqueous phase. Neutralization must be performed until the pH value of the aqueous phase remains between 0.5 and 3.0 and preferably between 2.2 and 2.7 to permit completion of the neutralization reaction.

Mineral acids such as nitric acid and hydrochloric acid cannot be employed to neutralize the emulsifier impurities when purifying the entire working solution since the presence of nitrate or chloride anions during the reaction will result in unfavorable side reaction products containing these anions.

Following neutralization of the emulsifier impurities, the turbid organic phase is permitted to separate from the aqueous phase. The resulting aqueous phase is discarded and the turbid organic phase is treated by conventional procedures to remove entrained water. The organic phase is then contacted with the absorbent materials described hereinbefore, without the necessity for removing dissolved water from the organic phase. It is not essential to remove the dissolved water from the organic phase prior to contacting the organic phase with the absorbent material since the solubility of water in the organic phase, that is the working solution, is only about 2.5 grams/liter compared to about 15 grams/liter in trioctyl phosphate purified separately.

The neutralized impurities are absorbed by the absorbent material leaving a substantially pure working solution having an interfacial tension greater than 20 dynes/cm. Hydrogen peroxide is then prepared from the purified working solution by the alternate reduction and oxidation of the substituted anthraquinone working compound. The hydrogen peroxide produced is then extracted from the working solution with an aqueous solvent having a broad pH range, that is 0.1 to 5.0, which pH range favors hydrogen peroxide removal and stability.

The invention will be better understood from a consideration of the following examples. All percentages are based upon weight unless otherwise indicated.

EXAMPLE 1

Process For Purifying Commercial Grade Trioctyl Phosphate According To The Invention Two (2) liters of commercial grade trioctyl phosphate having an interfacial tension of 5.5 dynes/cm was added to 500 milliliters of distilled water. The pH value of the water was adjusted to 2.5 with 85% phosphoric acid. The system was then stirred with a magnetic stirrer for 30 minutes. After stirring, the pH value of the water was 7.0 and the phases did not separate into distinct organic and aqueous phases. Additional 85% phosphoric acid was added while continuing the agitation. The phases separated immediately when the pH value of the aqueous phase was 2.5. The turbid trioctyl phosphate phase was separated from the clear aqueous phase and passed through a coalescing filter and treated with a desiccant to remove entrained and dissolved water. The acid treated trioctyl phosphate solvent had an interfacial tension of 22.5 dynes/cm, indicating that the emulsifier impurities were neutralized even though they were not removed. The trioctyl phosphate solvent was then passed three times through a one-inch diameter column packed with 155 cc of 14 × 28 mesh (U.S. Standard Sieve) activated alumina to absorb the neutralized impurities comprising dioctyl phosphoric acid and monooctyl phosphoric acid. Aluminum oxide fines were removed by filtering the purified trioctyl phosphate through a 0.45 micron filter. All operations were performed at room temperature (25° C). The resulting purified trioctyl phosphate solvent had an interfacial tension of 21.0 dynes/cm, no sodium values, and no detectable traces of dioctyl phosphoric acid or monooctyl phosphoric acid.

COMPARATIVE EXAMPLE A

Two (2) liters of commercial grade trioctyl phosphate employed in Example 1 was passed three times through a one-inch diameter column packed with 155 cc of 14 × 28 mesh (U.S. Standard Sieve) activated alumina without preliminary neutralization and dehydration treatments. The aluminum oxide fines were removed by filtering according to Example 1. The resulting trioctyl phosphate had an interfacial tension of 11.8 to 12.0 dynes/cm and over 100 ppm alkali metal salts of dioctyl phosphoric acid and monooctyl phosphoric acid.

EXAMPLE 2

Process For Purifying A Working Solution Containing Commercial Grade Trioctyl Phosphate According To The Invention An anthraquinone working solution was prepared by mixing together 7.41 liters of a commercially available, mixed aromatic solvent containing about 99.6 percent aromatics having a boiling point range of 182° to 204° C obtained from Shell Chemical Company and identified as Shell Sol AB and having an aromatic content of about 82.3% $C_8 - C_{12}$ alkyl benzene, 80% of which is $C_{10} - C_{11}$ alkyl benzene, and 13.3% cyclobenzene, 3.5% $C_{10}$ diaromatic (naphthalene), with 2 liters of commercial grade trioctyl phosphate having an interfacial tension of 5.5 dynes/cm. Thereafter 1,300 grams of 2-ethylanthraquinone was dissolved in the mixed solvent at 40° to 45° C. The solution was then filtered through a 2.0 micron filter to remove insolubles. After filtration, 2.5 liters of distilled water was added to the solution and the pH value of the aqueous phase was adjusted to between 2.2 and 2.5 with 85% phosphoric acid. The system was then stirred for 30 minutes during which time the pH value of the aqueous phase was kept below 2.7 by additional incremental additions of 85% phosphoric acid.

When stirring ceased the system immediately separated into two phases, an organic phase, that is the working solution, and an aqueous phase. The turbid organic phase was separated from the clear aqueous phase and passed through a coalescing filter to remove entrained water. The organic phase was then passed three times through a one-inch diameter column packed with 200 cc of 14 × 28 mesh (U.S. Standard Sieve) activated alumina to absorb the neutralized emulsifier impurities comprising dioctyl phosphoric acid and monooctyl phosphoric acid. The resulting purified working solution had an interfacial tension greater than 21 dynes/cm.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A process for purifying a working solution containing a substituted anthraquinone working compound used in preparing hydrogen peroxide, which comprises:
   a. preparing a working solution by dissolving said substituted anthraquinone working compound in a working solvent containing an anthraquinone solvent and trioctyl phosphate containing emulsifier impurities comprising alkali metal salts of dioctyl phosphoric acid and monooctyl phosphoric acid as the anthrahyroquinone solvent;
   b. contacting the working solution with a sufficient amount of an aqueous sulfuric acid or phosphoric acid solution to neutralize the emulsifier impurities and to provide a two-phase system having an organic phase containing the working solution and an aqueous phase wherein the pH value of the aqueous phase is between 0.5 and 3.0;
   c. separating the organic phase from the aqueous phase, and removing entrained water from the organic phase which contains the working solution and neutralized impurities; and
   d. contacting the organic phase with an absorbent material selected from the group consisting of activated alumina, silica gel, high surface area silica, zeolites and activated magnesia whereby the neutralized impurities are absorbed leaving a substantially pure working solution having an interfacial tension greater than 20 dynes/cm.

2. The process of claim 1 wherein the pH value of the aqueous phase in step b) is between 2.2 and 2.7.

3. The process of claim 1 which comprises preparing hydrogen peroxide from the purified working solution by alternate reduction and oxidation of the substituted anthraquinone working compound and extracting the hydrogen peroxide from the working solution with an aqueous solvent having a pH value of 0.1 to 5.0.

4. The process of claim 1 wherein the anthraquinone solvent is a polyalkylated benzene having a total of 9 to 11 carbon atoms.

5. A process for purifying trioctyl phosphate containing emulsifier impurities comprising alkali metal salts of dioctyl phosphoric acid and monooctyl phosphoric acid, which comprises:
   a. contacting said trioctyl phosphate with a sufficient amount of an aqueous mineral acid solution consisting essentially of sulfuric acid, phosphoric acid and nitric acid to neutralize the emulsifier impurities and to provide a two-phase system having an organic phase and an aqueous phase wherein the pH value of the aqueous phase is between 0.5 and 3.0;
   b. separating the organic phase from the aqueous phase and removing entrained and dissolved water from the organic phase which phase contains trioctyl phosphate and neutralized impurities comprising dioctyl phosphoric acid and monooctyl phosphoric acid; and
   c. contacting the organic phase with an absorbent material selected from the group consisting of activated alumina, silica gel, high surface area silica, zeolites, and activated magnesia whereby the neutralized impurities are absorbed leaving a substantially pure trioctyl phosphate having an interfacial tension of about 18 to about 24 dynes/cm.

6. The process of claim 1 wherein the pH value of the aqueous phase in step a) is between 2.2 and 2.7.

* * * * *

UNITED STATES PATENT OFFICE
CERTIFICATE OF CORRECTION

PATENT NO. : 3,996,341

DATED : December 7, 1976

INVENTOR(S) : NATHAN DEAN LEE

It is certified that error appears in the above-identified patent and that said Letters Patent are hereby corrected as shown below:

Column 4. line 6 "-50" should read -- -50 mesh--. Claim 5, Column 8, line 31 "silice gel" should read --silica gel--. Claim 6, Column 8, line 36 "claim 1" should read --claim 5--.

Signed and Sealed this

Twelfth Day of April 1977

[SEAL]

Attest:

RUTH C. MASON
*Attesting Officer*

C. MARSHALL DANN
*Commissioner of Patents and Trademarks*